(12) United States Patent
Schneider et al.

(10) Patent No.: US 9,643,390 B2
(45) Date of Patent: *May 9, 2017

(54) APPARATUSES AND METHODS FOR SEAMING SUBSTRATES

(71) Applicant: The Procter & Gamble Company, Cincinnati, OH (US)

(72) Inventors: Uwe Schneider, Cincinnati, OH (US); Horst Blessing, Cincinnati, OH (US); Hans Adolf Jackels, Mechernich (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/641,898

(22) Filed: Mar. 9, 2015

(65) Prior Publication Data

US 2015/0174875 A1    Jun. 25, 2015

Related U.S. Application Data

(63) Continuation of application No. 13/401,907, filed on Feb. 22, 2012, now Pat. No. 9,005,392.

(51) Int. Cl.
*B32B 37/00* (2006.01)
*B32B 37/06* (2006.01)
(Continued)

(52) U.S. Cl.
CPC ...... *B32B 37/065* (2013.01); *A61F 13/15739* (2013.01); *A61F 13/49058* (2013.01);
(Continued)

(58) Field of Classification Search
CPC ..... A61F 13/15739; A61F 2013/15886; B32B 37/065; B32B 37/30; B32B 37/0084;
(Continued)

(56) References Cited

U.S. PATENT DOCUMENTS 3,322,584 A * 5/1967 Welin-Berger ......... B29C 65/10
                                                    156/251
3,468,096 A * 9/1969 Franz .................... A47L 17/08
                                                    15/104.93
(Continued)

FOREIGN PATENT DOCUMENTS

JP          08-56988        3/1996
WO     WO 2011/156299 A1   12/2011

OTHER PUBLICATIONS

International Search Report, PCT/US2013/026978, dated May 29, 2013, 10 pages.

*Primary Examiner* — John Goff
(74) *Attorney, Agent, or Firm* — Sarah M. DeCrostofaro; Abbey A. Lopez

(57) ABSTRACT

A method of joining substrate portions includes positioning the substrate portions such that the substrate portions overlap at an overlap area. The substrate portions each have a melting temperature and an outer surface. A fluid is heated to a temperature sufficient to at least partially melt the substrate portions. A jet of the heated fluid is directed from a fluid orifice onto the substrate portions at the overlap area. The heated fluid penetrates at least one of the outer surfaces of the substrate portions. The substrate portions are at least partially melted using the heated fluid. The substrate portions are compressed using a pressure applying surface adjacent the fluid orifice to join the substrate portions together at the overlap area.

5 Claims, 16 Drawing Sheets

(51) Int. Cl.

| | | |
|---|---|---|
| *A61F 13/496* | (2006.01) | |
| *A61F 13/15* | (2006.01) | |
| *B32B 37/10* | (2006.01) | |
| *B32B 37/30* | (2006.01) | |
| *B32B 38/00* | (2006.01) | |
| *A61F 13/49* | (2006.01) | |
| *B29C 65/10* | (2006.01) | |
| *B29C 65/00* | (2006.01) | |
| *B29L 31/48* | (2006.01) | |

(52) U.S. Cl.
CPC ......... *A61F 13/4963* (2013.01); *B29C 65/10* (2013.01); *B29C 66/1122* (2013.01); *B29C 66/21* (2013.01); *B29C 66/43* (2013.01); *B29C 66/431* (2013.01); *B29C 66/73116* (2013.01); *B29C 66/8226* (2013.01); *B29C 66/8242* (2013.01); *B29C 66/8351* (2013.01); *B29C 66/83221* (2013.01); *B29C 66/83411* (2013.01); *B29C 66/83511* (2013.01); *B32B 37/06* (2013.01); *B32B 37/10* (2013.01); *B32B 37/30* (2013.01); *B32B 38/0004* (2013.01); *B29C 66/133* (2013.01); *B29C 66/71* (2013.01); *B29C 66/729* (2013.01); *B29C 66/7294* (2013.01); *B29C 66/93411* (2013.01); *B29L 2031/4878* (2013.01); *B32B 2309/02* (2013.01); *B32B 2309/04* (2013.01); *B32B 2309/12* (2013.01); *Y10T 156/1052* (2015.01); *Y10T 156/1054* (2015.01); *Y10T 156/17* (2015.01)

(58) Field of Classification Search
CPC ..... B32B 37/1045; B32B 66/21; B29C 65/10; B29C 65/7471; B29C 65/12; Y10T 156/1054
USPC ........................................................ 156/324
See application file for complete search history.

(56) References Cited

U.S. PATENT DOCUMENTS

| | | | |
|---|---|---|---|
| 3,860,003 A | | 1/1975 | Buell |
| 4,610,678 A | | 9/1986 | Weisman et al. |
| 4,619,649 A | * | 10/1986 | Roberts ................. A61F 5/4401 604/385.29 |
| 4,673,402 A | | 6/1987 | Weisman et al. |
| 4,695,278 A | | 9/1987 | Lawson |
| 4,704,115 A | | 11/1987 | Buell |
| 4,795,454 A | | 1/1989 | Dragoo |
| 4,834,735 A | | 5/1989 | Alemany et al. |
| 4,886,632 A | * | 12/1989 | Van Iten ........... A61F 13/15577 156/252 |
| 4,888,231 A | | 12/1989 | Angstadt |
| 4,909,803 A | | 3/1990 | Aziz et al. |
| 4,919,738 A | * | 4/1990 | Ball ..................... B29C 66/1122 156/290 |
| 5,188,691 A | | 2/1993 | Caputo |
| 5,562,646 A | | 10/1996 | Goldman et al. |
| 5,599,335 A | | 2/1997 | Goldman et al. |
| 5,628,097 A | | 5/1997 | Benson et al. |
| 5,669,894 A | | 9/1997 | Goldman et al. |
| 5,779,831 A | | 7/1998 | Schmitz |
| 5,916,661 A | | 6/1999 | Benson et al. |
| 5,935,363 A | * | 8/1999 | Gilman ............... A61F 13/0276 156/199 |
| 6,010,653 A | * | 1/2000 | Menon .................... B29C 41/16 156/308.6 |
| 6,107,539 A | | 8/2000 | Palumbo et al. |
| 6,248,195 B1 | * | 6/2001 | Schmitz ................ A61F 13/539 156/290 |
| 6,545,197 B1 | | 4/2003 | Muller et al. |
| 6,790,798 B1 | | 9/2004 | Suzuki et al. |
| 6,800,162 B2 | | 10/2004 | Kannankeril et al. |
| 7,569,039 B2 | | 8/2009 | Matsuda et al. |
| 7,587,966 B2 | | 9/2009 | Nakakado et al. |
| 8,778,127 B2 | | 7/2014 | Schneider |
| 9,005,392 B2 | * | 4/2015 | Schneider ........... A61F 13/4963 156/290 |
| 2004/0097895 A1 | | 5/2004 | Busam et al. |
| 2004/0107764 A1 | | 6/2004 | Yan |
| 2004/0158212 A1 | | 8/2004 | Ponomarenko et al. |
| 2010/0096065 A1 | | 4/2010 | Yamamoto |
| 2011/0151171 A1 | | 6/2011 | Biegler et al. |
| 2012/0021186 A1 | | 1/2012 | Schneider |
| 2012/0061015 A1 | | 3/2012 | LaVon et al. |
| 2012/0061016 A1 | | 3/2012 | LaVon et al. |
| 2013/0213547 A1 | | 8/2013 | Schneider et al. |
| 2013/0218116 A1 | | 8/2013 | Schneider et al. |
| 2014/0110053 A1 | | 4/2014 | Ordway et al. |

* cited by examiner

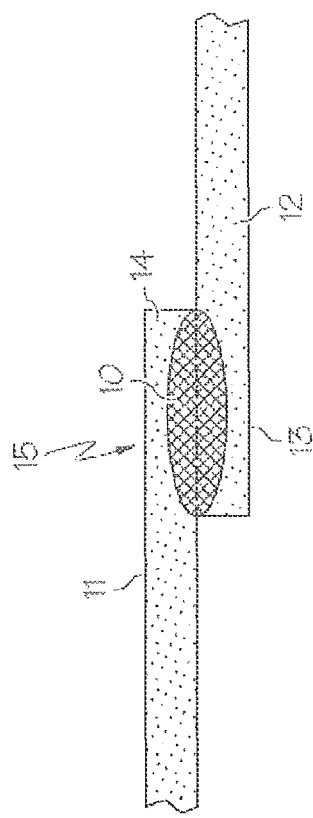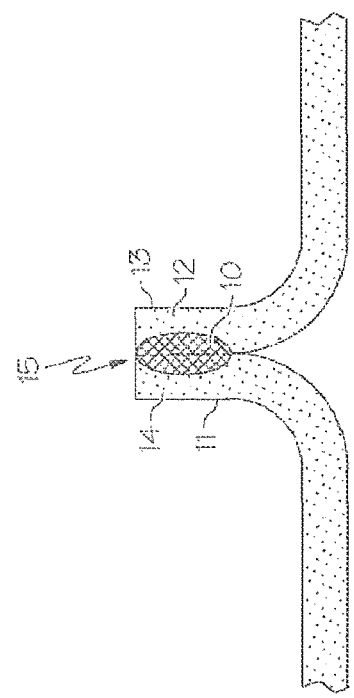

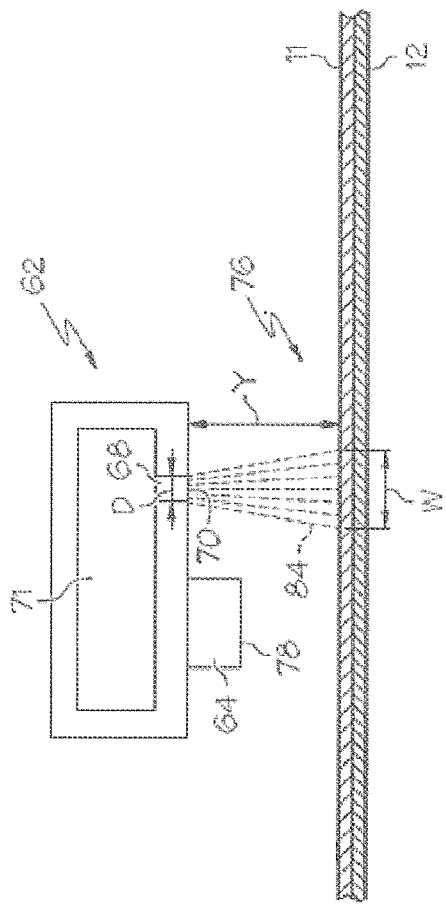
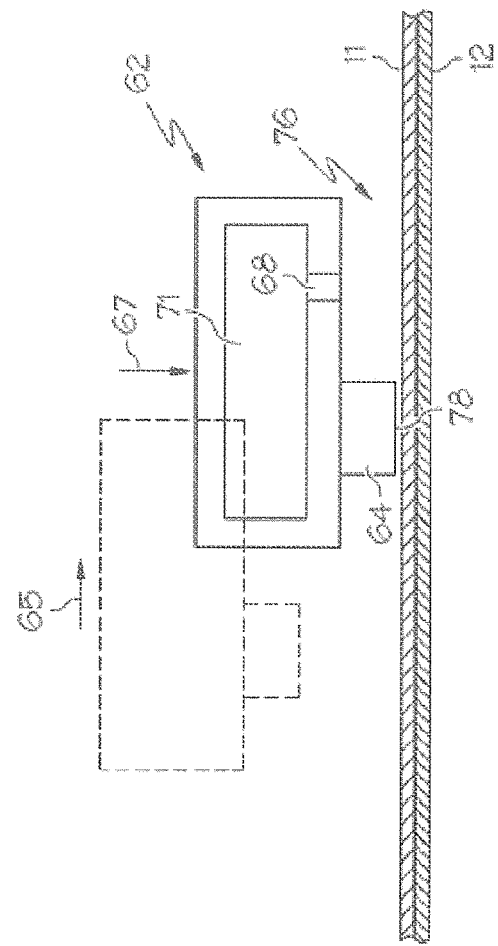

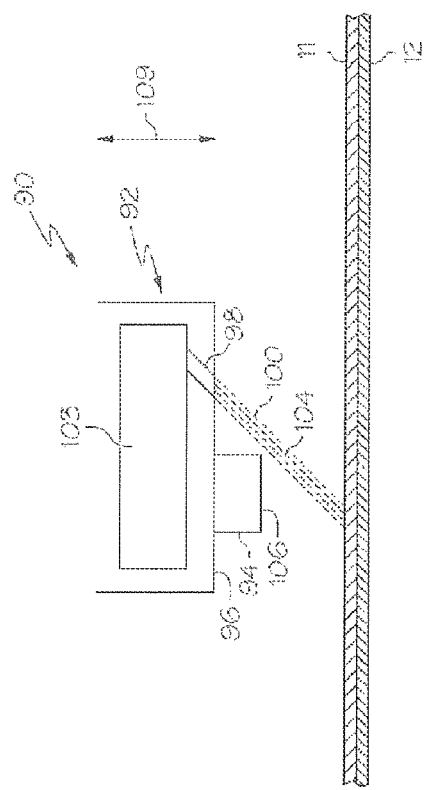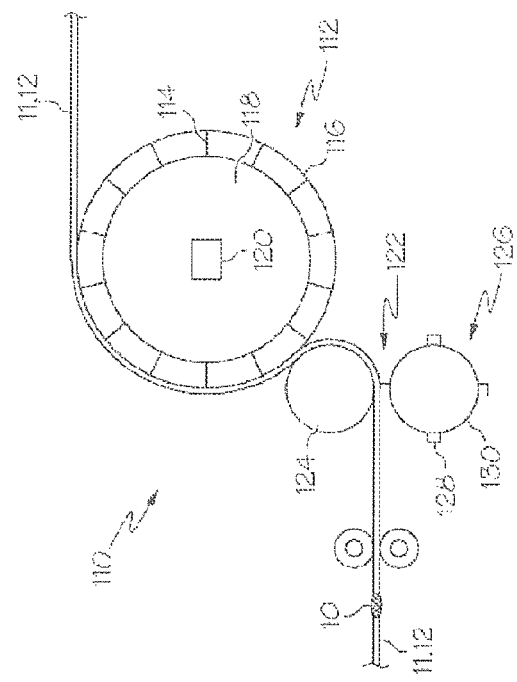

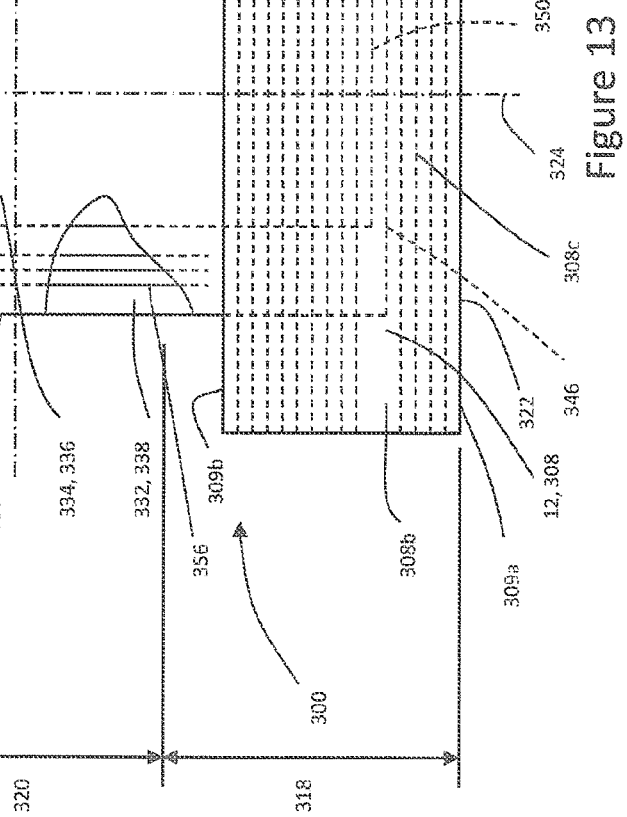
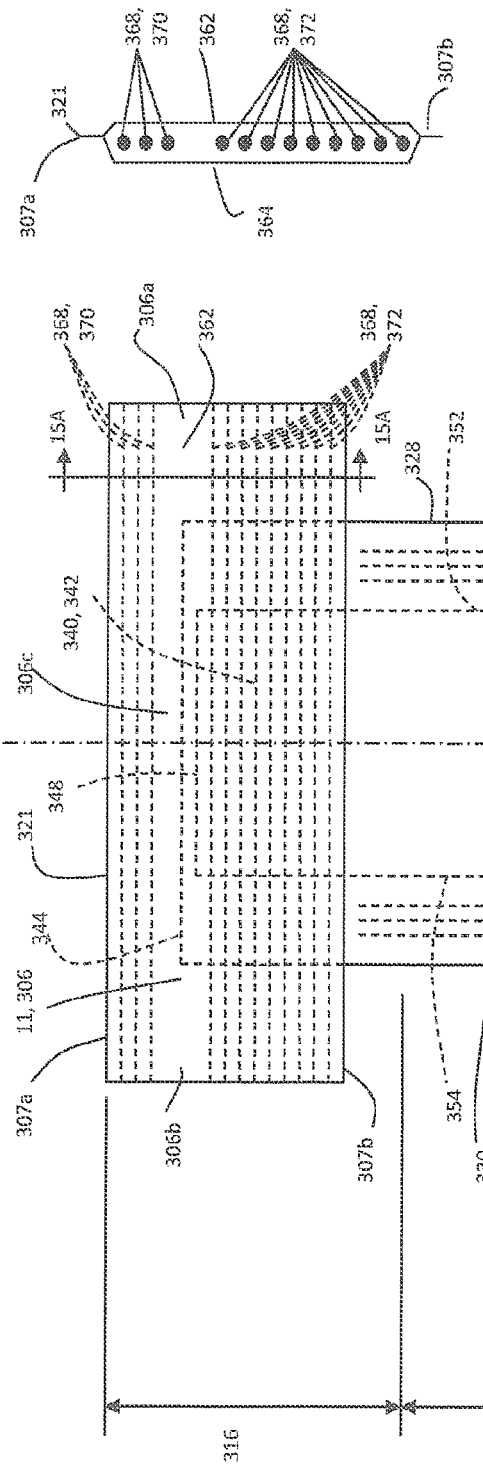
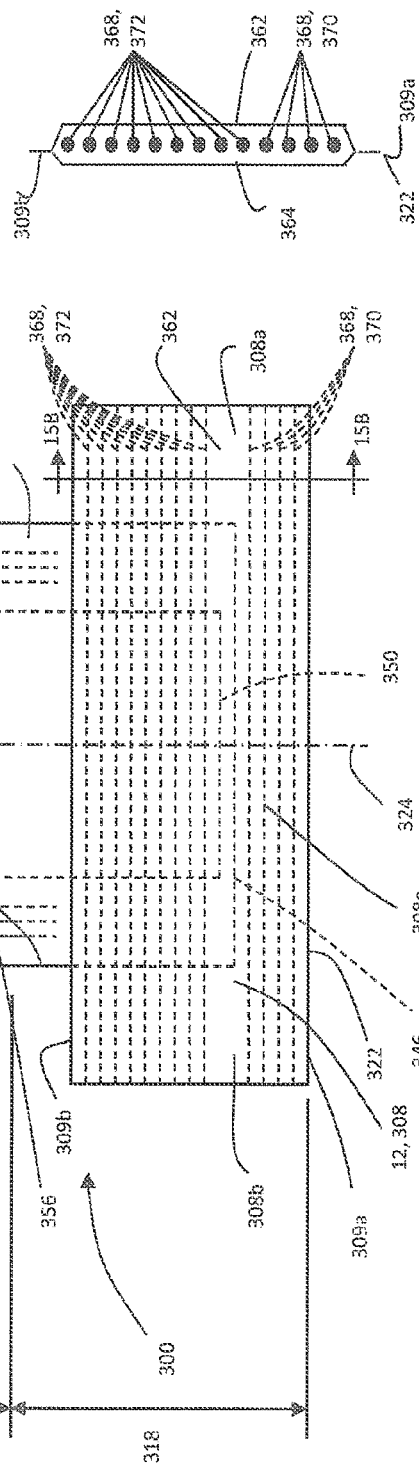
Figure 13
Figure 15A
Figure 15B

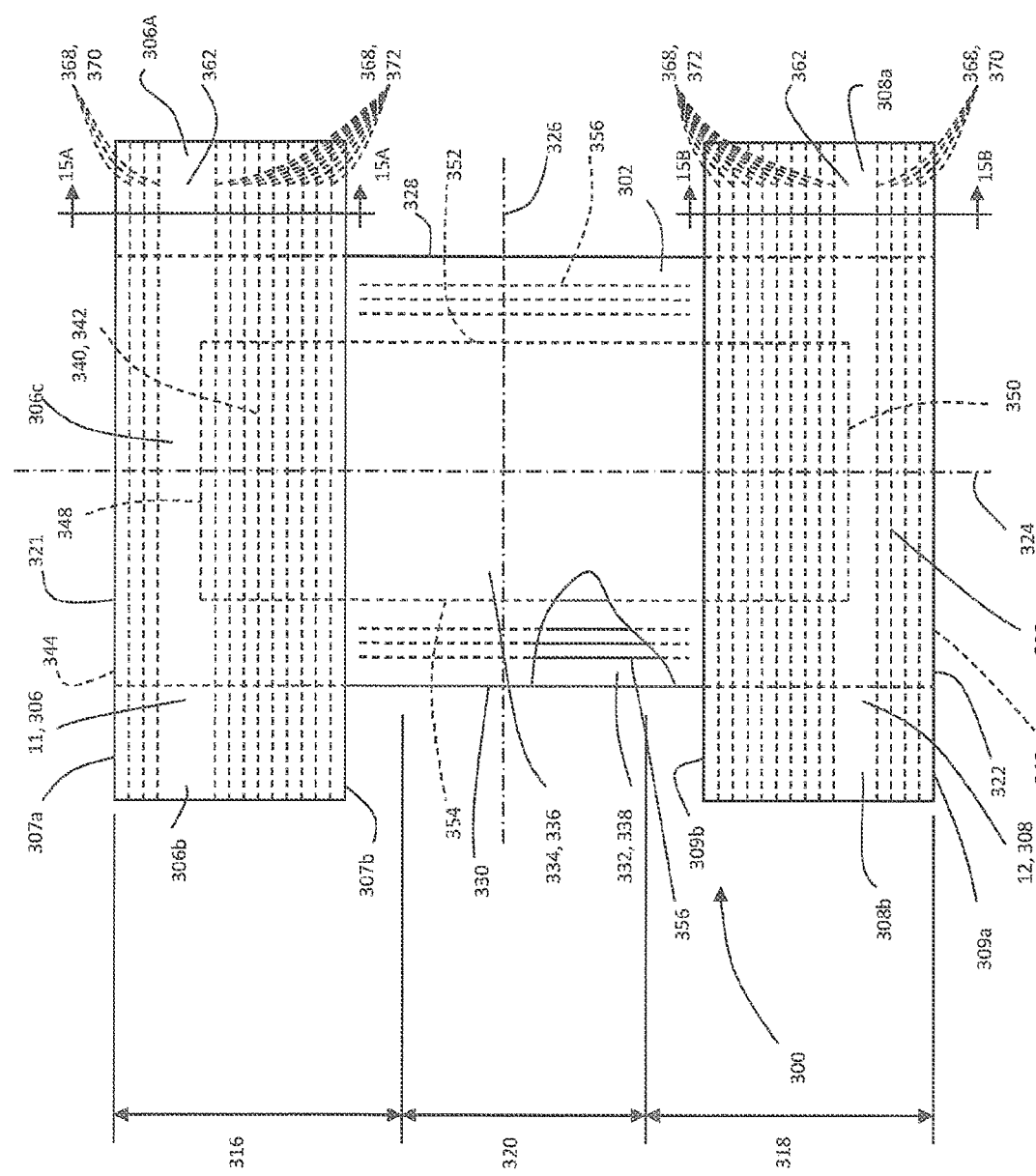

APPARATUSES AND METHODS FOR SEAMING SUBSTRATES

CROSS REFERENCE TO RELATED APPLICATION

This application is a continuation of application Ser. No. 13/401,907 filed on Feb. 22, 2012, which is incorporated herein by reference.

TECHNICAL FIELD

The present disclosure relates to methods for manufacturing absorbent articles, and more particularly, to apparatuses and methods for seaming two or more partially meltable materials.

BACKGROUND

Disposable absorbent articles, in particular, disposable diapers, are designed to be worn by people experiencing incontinence, including infants and invalids. Such diapers are worn about the lower torso of the wearer and are intended to absorb and contain urine and other bodily discharges, thus preventing the soiling, wetting, or similar contamination of articles that may come into contact with a diaper during use (e.g., clothing, bedding, other people, etc.). Disposable diapers are available in the form of pull-on diapers, also referred to as training pants, having fixed sides. The fixed sides may be manufactured by joining side panels of the front portion of the diaper to side panels of the rear portion of the diaper. For joining purposes, the contacting surfaces of the side panels may be at least partially melted by directing heated fluid to areas of the contacting surfaces. Pressure may then be applied to the partially melted areas.

Consequently, during the process of joining substrates together, it would be beneficial to provide methods and apparatuses for more precisely directing the heated fluid and applying pressure to the partially melted areas of the substrates.

SUMMARY

Aspects of the present disclosure involve apparatuses and methods for manufacturing absorbent articles, and more particularly, methods for seaming substrates during the manufacture of disposable absorbent articles. Particular embodiments of methods of manufacture disclosed herein provide for forming side seams in various types of diaper configurations. While the present disclosure relates mainly to forming side seams in diaper pants, it is to be appreciated that the methods and apparatuses disclosed herein can also be applied to other seams used on diapers as well as other types of absorbent articles.

In one embodiment, a method for forming a seam includes the steps of: providing an anvil block; providing a forming block adjacent the anvil block, the forming block comprising a face, a pressure applying member extending outwardly from the face toward the anvil block, and a fluid orifice in the face spaced laterally from the pressure applying member; advancing a first substrate in a machine direction between the forming block and the anvil block with a separation distance between the fluid orifice and the first substrate; advancing a second substrate in the machine direction wherein the first substrate is between the second substrate and the forming block; controlling the separation distance between the first substrate and the fluid orifice; heating a fluid to a temperature sufficient to at least partially melt the substrates; directing a jet of the heated fluid through the fluid orifice and onto an overlap area of the first and second substrates; partially melting the overlap area; and compressing the overlap area between the pressure applying member and the anvil block.

In another embodiment, the method for forming a seam includes the steps of: providing an anvil block; providing a forming block adjacent the anvil block, the forming block comprising a face, a pressure applying member extending outwardly from the face toward the anvil block, and a fluid outlet extending through a portion of the forming block and spaced laterally from the pressure applying member; advancing a first substrate in a machine direction between the forming block and the anvil block with a separation distance between the fluid orifice and the first substrate; advancing a second substrate in the machine direction wherein the first substrate is between the second substrate and the forming block; controlling the separation distance between the first substrate and the fluid orifice; heating a fluid to a temperature sufficient to at least partially melt the substrates; directing a jet of the heated fluid through the fluid orifice and onto an overlap area of the first and second substrates; partially melting the overlap area; and compressing the overlap area between the pressure applying member and the anvil block.

In another embodiment, a method for forming a seam includes the steps of: providing an anvil block; providing a forming block adjacent the anvil block, the forming block comprising a face, a pressure applying member extending outwardly from the face toward the anvil block, and a fluid outlet combined with the pressure applying member; advancing a first substrate in a machine direction between the forming block and the anvil block with a separation distance between the fluid orifice and the first substrate; advancing a second substrate in the machine direction wherein the first substrate is between the second substrate and the forming block; controlling the separation distance between the first substrate and the fluid orifice; heating a fluid to a temperature sufficient to at least partially melt the substrates; directing a jet of the heated fluid through the fluid orifice and onto an overlap area of the first and second substrates; partially melting the overlap area; and compressing the overlap area between the pressure applying member and the anvil block.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

FIG. 1A illustrates an embodiment of substrate portions joined at a seam.

FIG. 1B illustrates another embodiment of substrate portions joined at a seam.

FIG. 6A illustrates the seaming apparatus of FIG. 5 in use.

FIG. 6B illustrates the seaming apparatus of FIG. 5 in use.

FIG. 7 is a simplified, schematic drawing of another embodiment of a seaming apparatus useful for joining two or more substrate portions.

FIG. 8 is a simplified, schematic drawing of another embodiment of a seaming apparatus useful for joining two or more substrate portions.

FIG. 13 is a partially cut away plan view of the diaper pant shown in FIG. 1.

FIG. 14 is a partially cut away plan view of a second embodiment of a diaper pant.

FIG. 15A is a cross-sectional view of the diaper pants of FIGS. 13 and 14 taken along line 15A-15A.

FIG. 15B is a cross-sectional view of the diaper pants of FIGS. 13 and 14 taken along lines 15B-15B.

DETAILED DESCRIPTION

Figure 1C:
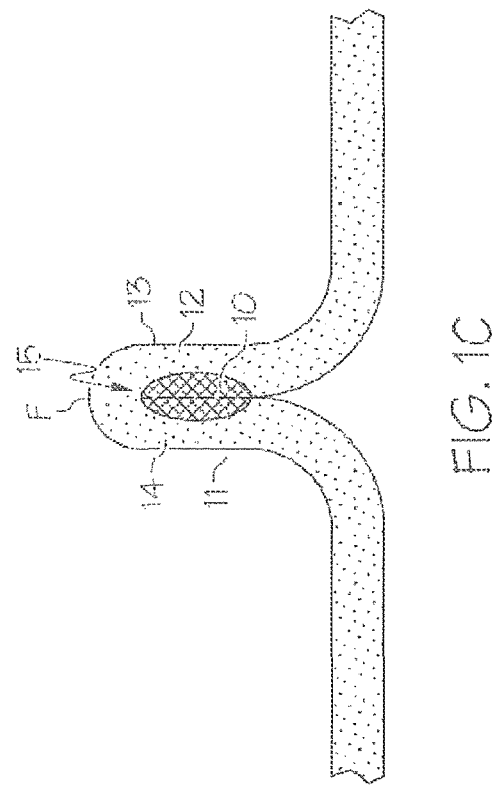
FIG. 1C illustrates another embodiment of substrate portions joined at a seam.

The methods and apparatuses described herein relate to seaming substrates. In general, portions of substrates may be overlapped and a jet of heated fluid is delivered from an orifice to at least partially melt the overlapping substrate portions. More particularly, the jet of heated fluid penetrates the substrate portions and at least partially melts the overlapping substrate portions where the substrate portions interface at an overlap area. The location of the substrate portions relative to the orifice may be controlled such that the substrate portions are held a predetermined distance away from the orifice during the heating operation. Pressure may then be applied at the overlap area thereby joining the substrate portions together. In all the embodiments described herein, the fluid may include ambient air or other gases.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

As used herein, the term "joining" describes a configuration whereby a first element is directly secured to another element by affixing the first element directly to the other element.

As used herein, the term "substrate" is used herein to describe a material which is primarily two-dimensional (i.e. in an XY plane) and whose thickness (in a Z direction) is relatively small (i.e. 1/10 or less) in comparison to its length (in an X direction) and width (in a Y direction). Non-limiting examples of substrates include a substrate, layer or layers or fibrous materials, nonwovens, films and foils such as polymeric films or metallic foils. These materials may be used alone or may comprise two or more layers laminated together. As such, a web is a substrate.

As used herein, the term "pull-on diaper" refers to a garment that is generally worn by infants and sufferers of incontinence, which is pulled on like pants. It should be understood, however, that the present disclosure is also applicable to other absorbent articles, such as taped diapers, incontinence briefs, feminine hygiene garments, and the like, including absorbent articles intended for use by infants, children, and adults.

As used herein, the term "inboard" refers to a first element or material which is nearer the lateral or longitudinal centerline of an article relative to a second element or material, the second element or material being "outboard" of the first.

As used herein, the term "porous" refers to a material having an air permeability of at least 30 $cm^3/cm^2/sec$ when tested according to the standard test method for Permeability to Air; Cloth; Calibrated Orifice Method, as described in Method 5450 of Federal Test Method Standard No. 191A.

As used herein, the term "at least partially melted" refers to materials at least a portion of which have reached at least a softening point temperature, but have not reached a melt point temperature. "Melted" also refers, in its ordinary sense, to materials which have exceeded their melt point temperatures over at least a portion of the material.

In some aspects, the present disclosure relates to seams, methods for making seams, articles comprising a seam, and methods for making articles comprising a seam. As described in greater detail below, a seam may be formed between two substrates, each substrate comprising one or more meltable components. A seam may also be formed between portions of the same substrate that is, for example, folded along a fold line formed between the two substrate portions. The substrate portions to be seamed may be positioned adjacent one another, and heated to at least a softening temperature, or a melting temperature, to at least partially melt one or both of the substrate portions. The substrate portions may be compressed after heating. The description which follows describes generally seams, methods for making seams and apparatus for making seams. While various embodiments are separately described and illustrated, it is to be appreciated that various aspects of the different embodiments can be combined to produce yet further embodiments, which may not be described explicitly for the purpose of brevity.

Schematic, fragmentary side elevational views of two substrate portions to be joined are shown in FIGS. 1A, 1B and 1C. At least two substrate portions 11, 12 are arranged in an adjacent manner to form a seam 10. The seam 10 comprises outer surfaces 13, 14 and an area of overlap 15 between the substrates 11, 12. FIG. 1A shows a configuration herein referred to as an overlap seam, wherein two or more materials are joined along adjacent, overlapping surfaces. FIG. 1B shows a configuration herein referred to as a butt seam, wherein two or more materials are joined at or near their edges and the materials are folded back, away from the seam. FIG. 1C illustrates substrate portions 11 and 12 that are part of the same continuous substrate that are folded at a fold line F and overlapped.

The joining of at least two substrate portions 11 and 12 that are arranged in an adjacent manner to form a seam 10, such as illustrated in FIG. 1A or 1B, may comprise providing a first substrate and folding the substrate to provide the substrate portions 11 and 12, where the substrate portions have a melting temperature and an outer surface 13, 14, the melting temperatures of the first 11 and second substrates 12 being substantially the same or substantially different. The seaming operation may be accomplished in an integrated folding-and-sealing unit, as described, for example, in U.S. Pat. No. 5,779,831 to Schmitz. In some embodiments, the substrate portions 11 and 12 may be part of different, separate substrates that are overlapped. The seaming operation may further comprise a step of placing the substrate portion 11 adjacent the substrate portion 12 to form the overlap area 15. A fluid may be sufficiently heated to enable at least a partial melting of the substrate portions 11, 12. A jet of the heated fluid may be directed toward at least one of the outer surface 13 of the substrate portion 11 and the outer surface 14 of the substrate portion 12. The fluid may be allowed to penetrate the substrate portions 11 and 12 such that at least a portion of each of the substrate portions 11 and 12 is melted in the overlap area 15. The heated fluid, at a controlled temperature and pressure, may pass from the fluid outlet, leading to the formation of controlled and concentrated jets of heated fluid, which are directed toward outer surfaces 13, 14 of substrate portions 11, 12 to be joined.

By controlled, it is meant that the temperature and pressure are maintained within a specified range once the nominal set points are selected. For example, a set point may be selected from the ranges discussed above, and the temperature may then be maintained in a fixed range around the nominal set point, such as ±30° C., and the pressure may be maintained in a fixed range around the nominal set point, such as ±1 bar. The acceptable range will depend on the relationship between the properties, such as softening point and/or melting temperature, of the materials to be joined and the nominal set point selected. For example, a nominal set point above the melting temperature of one or more of the materials to be joined may require a tighter control range than a nominal set point well below the melting temperature of one or more material to be joined. The control range may be asymmetrical about the nominal set point. By sufficiently heating, it is meant that the fluid is heated to a temperature that will enable at least partial melting, or at least softening, of the substrate or substrates. Sufficient heating may vary with the materials and equipment used. For example, if the heated fluid is applied to the substrate or substrates almost immediately, with little or no time to cool, the fluid may be heated to approximately the softening point or approximately the melting point of the substrate or substrates. If the heated fluid is directed to the substrate or substrates over some gap in time or distance, such that the heated fluid may cool somewhat before interacting with the substrate or substrates, it may be necessary to heat the fluid above, possibly significantly above, the softening point or melting point of the substrate or substrates.

The fluid may also be delivered to outer surfaces 13, 14 with a pulsed application. The impact of the jet of heated fluid may be adjusted such that both the energy introduced by the jet plus the energy introduced by other means such as the heated anvil (if the anvil is heated), jet nozzle surface, deformation of substrate portions 11, 12, and the internal friction of substrate portions 11, 12 are sufficient to at least partially melt the meltable components in substrate portions 11, 12 to create a certain tackiness, which will form a strong joint at area of overlap 15 upon compression. The melting of the meltable components may occur in a non-uniform manner throughout substrate portions 11, 12.

The duration of energy transfer in the process described herein may be a dynamic process, and may create a temperature gradient across the cross sections of the meltable components. That is, the core of the meltable components may remain solid while the exterior surface of the meltable components melt or come close to melting. Even below the melting temperature, the exterior surface may reach a softening point, such that plastic deformation of the material may occur at a much lower load than for the same material at ambient temperature. Thus, if one or more of the materials to be joined in seam 10 have a softening point, the process may be adjusted to achieve a temperature in at least a portion of substrate portions 11, 12 between the softening point and the melting point. The use of a temperature at or above the softening point but below the melting point of one or more of the meltable components may allow for the creation of a strong bond between substrate portions 11, 12 with reduced disruption to the structure of the meltable components e.g., attenuating or otherwise weakening the meltable components.

As discussed in more detail below, methods of joining at least two substrate portions may further comprise the step of compressing seam 10 with the one or more pressure applying member while the meltable components are at least partially melted, and/or in the tacky state. The temperature of the pressure applying members may be at least below the melting point of seam 10. In some embodiments, the pressure applying member may be heated. The tackiness property of the meltable components permits the joining of substrate portions 11, 12 and thus, the accumulation of melted substrate material may be reduced or avoided. Such melted material may form hard, raspy protuberances on the outer surfaces of seam 10 upon solidification. The pressure applying members may be designed according to aesthetic criteria, for example, to provide discrete, shaped points where substrate portions 11, 12 are joined. Discrete compression points may also make the seam easier to open, if desired. The compression points may generally take the shape and spacing of the pressure applying surfaces. As one example, the pressure applying members may be generally oval, or may have any other geometric or decorative shape consistent with the desired removal force and removal force perception. The pressure applying members may be regularly or irregularly spaced, and may be oriented in various directions.

In some embodiments, a method as described herein is part of a method for making an absorbent article. For example, a method for making an absorbent article may comprise providing a first substrate portion 11 and a second substrate portion 12, each of the first 11 and second substrate portions 12 having a melting temperature and an outer surface 13, 14, the melting temperatures of the first 11 and second substrate portions 12 being substantially the same or substantially different. The first substrate portion 11 may be placed adjacent at least the second substrate portion 12 to form an overlap area 15. A fluid may be sufficiently heated to enable at least a partial melting of the first and second substrate portions 11, 12. A jet of the heated fluid may be directed toward at least one of the outer surface 13 of the first substrate portion 11 and the outer surface 14 of the second substrate portion 12. The fluid may be allowed to penetrate the first 11 and second substrate portions 12 such that at least a portion of each of the first 11 and second substrates 12 is melted in the overlap area 15. The first substrate portion 11 and the second substrate portion 12 may comprise a side panel, a front portion, a rear portion, or a combination thereof. As discussed in more detail below, the absorbent article may be a pull-on diaper, as one example. The first and second substrate portions may be nonwoven materials. The first and second substrate portions may further comprise an elastic film. A method for making an absorbent article may further comprise compressing overlap area 15. The compression of overlap area 15 may be performed after the partial melting of substrate portions 11 and 12 in the overlap area 15. For example, the compression of overlap area 15 may occur within 5 milliseconds, or 10 milliseconds, or 50 milliseconds of the partial melting of substrate portions 11 and/or 12. In some embodiments, the overlap area 15 may be compressed through multiple iterations. Once compressed, the substrate portions 11 and 12 may be cut into individual articles, using, for example, a mechanical cutting device such as a flex blade or die knife. In some embodiments, it is to be appreciated that the substrate portions 11 and 12 are compressed and cut in a single step.

Substrate portions 11 and 12 may be non-woven substrates with a basis weight ranging from 10 to 500 grams per square meter, containing fibers ranging from microfibers of less than one denier to conventional fibers ranging from 1 to 7 denier. The non-woven substrates may also contain elastic materials in the form of strands. Based in part on the thickness of the substrates, the interval of time required to join the substrates 11, 12 with this method may range from 5 to 2000 milliseconds. In some embodiments, 30 to 250 milliseconds may be used for heating and 5 to 250 milliseconds may be used for compression/cooling. In some embodiments, the compression step may be very short, nearly instantaneous. The time intervals used may vary with the nominal pressure and temperature selections. A higher processing time may be tolerated by the materials without damage at lower pressure and/or temperature, whereas higher pressure and/or temperature may be used with shorter processing times.

At least one of the substrate portions 11 and 12 may comprise sufficient meltable material that the substrate portion is susceptible to being thermally joined to another substrate portion. Substrate portions 11, 12 may be porous—air permeable, fluid permeable or vapor permeable—and substrate portion 11, substrate portion 12, or both substrate portions 11 and 12 may comprise meltable components. Substrate portions 11, 12 may be woven or non-woven, and may comprise fibers or polymeric binders, natural fibers such as cellulose—wood pulp, cotton, jute, hemp; synthetic fibers such as rayon, polyester, polyolefin, acrylic, polyamide, aramid, polytetrafluroethylene metal, polyimide, polypropylene, polyethylene; or binders such as bicomponent fibers, copolymer polyester, polyvinyl chloride, polyvinyl acetate/chloride copolymer, copolymer polyamide, polyurethane-polyurea copolymer. The substrate portions 11 and 12 may comprise blends of materials wherein some of the constituent materials are not meltable. Substrate portions 11, 12 may be of the same or different materials. Substrate portions 11, 12 each have a melting temperature, and the melting temperature of the substrate portions 11, 12 may be different or substantially the same. The melting temperatures are substantially the same if they are within 30° C. of each other. The melting temperatures of substrate portions 11, 12 may be within 10° C. of each other, or within 5° C. of each other. In some embodiments, the melting temperatures of substrate portions 11, 12 are the same. As the difference between the melting temperatures of substrate portions 11, 12 decreases, the ability to control the seam may increase.

The seaming process doses and disperses thermal energy in and around the overlap area where a bond will be formed. In some instances, the lower the thermal energy delivered to form the bond, the less likely the process is to damage nearby materials or to impact layers adjacent the intended bond site. A jet of heated fluid, such as air for example, may be dispersed through porous layers, or, where the melting temperature of substrate portions 11, 12 is not the same, hot air may be used to form a hole through the outer layer, allowing penetration of the hot air to the inner substrate portion. Where substrate portions 11, 12 are each porous and the substrate portions 11, 12 have substantially the same melting temperature, a relatively low temperature, low pressure air stream may be used, resulting in little damage to the fibers in and around the bond area. In some instances, if one of the substrate portions 11, 12, or another layer of material intervening between the hot air source and substrate portions 11, 12, is not porous or has a melting temperature which is not substantially the same as the other layers, a relatively high temperature, high pressure air stream may be needed.

Figure 2:
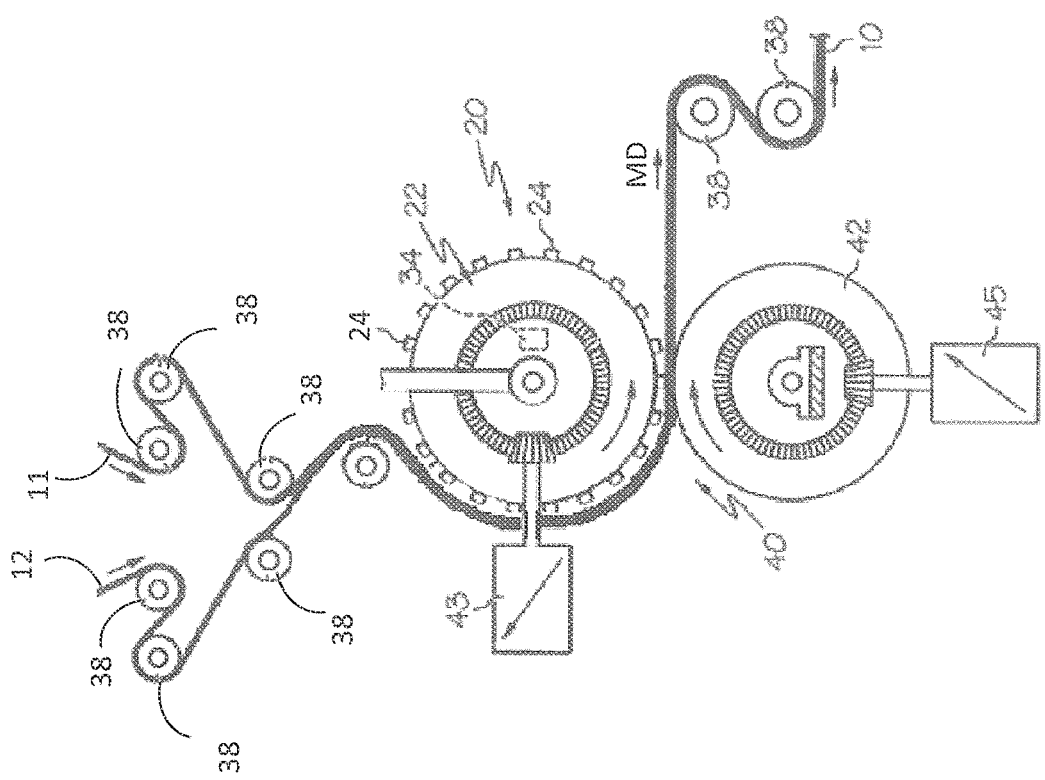
FIG. 2 is a simplified, schematic drawing of an embodiment of a rotary seaming apparatus useful for joining two or more substrate portions.

Referring to FIG. 2, a simplified, diagrammatic drawing of a rotary seaming apparatus 20 may be used for joining the substrate portions 11 and 12 to form the seam 10. The rotary seaming apparatus 20 includes a forming cylinder 22 with pressure applying members 24 extending radially outwardly from an outer circumferential surface 26 of the forming cylinder 22. It is to be appreciated that the forming cylinder 22 may include one or more pressure applying members 24. The pressure applying members 24 may include fluid outlets 28, each fluid outlet 28 including a fluid orifice 30. The fluid outlet 28 is in fluid communication with a fluid chamber 32 providing a pressurized fluid source for delivery of heated, pressurized fluid, such as air for example, to the fluid outlet 28. In some embodiments, a heating device 34 may be provided for heating the fluid within the fluid chamber 32. In some embodiments, a valve 36 may control egress of fluid from the fluid chamber 32 and into the fluid outlet 28.

As shown in FIG. 2, driving rolls 38 may be used to advance the substrate portions 11 and 12 in a machine direction MD onto the forming cylinder 22. The substrate portions 11 and 12 wrap around the outer circumferential surface of the forming cylinder 22 as it rotates. Once received on the forming cylinder 22, heated, pressurized fluid is released from the fluid outlets to heat the substrate portions 11 and 12 as the forming cylinder rotates. The at least partially melted substrate portions advance through a nip 40 between the forming cylinder 22 and an anvil cylinder 42. The anvil cylinder 42 may be positioned relative to the forming cylinder 22 such that a pressure applying surface 44 of the pressure applying member 24 can compress the substrate portions 11 and 12 together at the area of overlap 15 as the substrate portions 11 and 12 advances through the nip 40. In some embodiments, the height of nip 40 may be adjusted to control the pressure applied to the substrate portions 11 and 12 through the pressure applying members 24. The pressure applied to the substrate portions 11 and 12 may, for example, be in the range of $1 \times 10^5$ Newtons per square meter to $1 \times 10^8$ Newtons per square meter.

Although not shown in the figures, it is to be appreciated that the upstream ends or sources of the substrate portions 11, 12 and downstream destination of the seam 10 may have various different configurations. For example, the substrate portions 11 and 12 may originate in roll form, and there may be provided upstream unwinding, splicing and/or folding means to enable forwarding continuous lengths of such substrates through joining means and/or converters to make substrate structures. Further, although the apparatus 20 is described herein as comprising forming cylinder 22 and anvil cylinder 42, such description is not intended in any way to limit the method described to an apparatus comprising cylinders.

Figure 3:
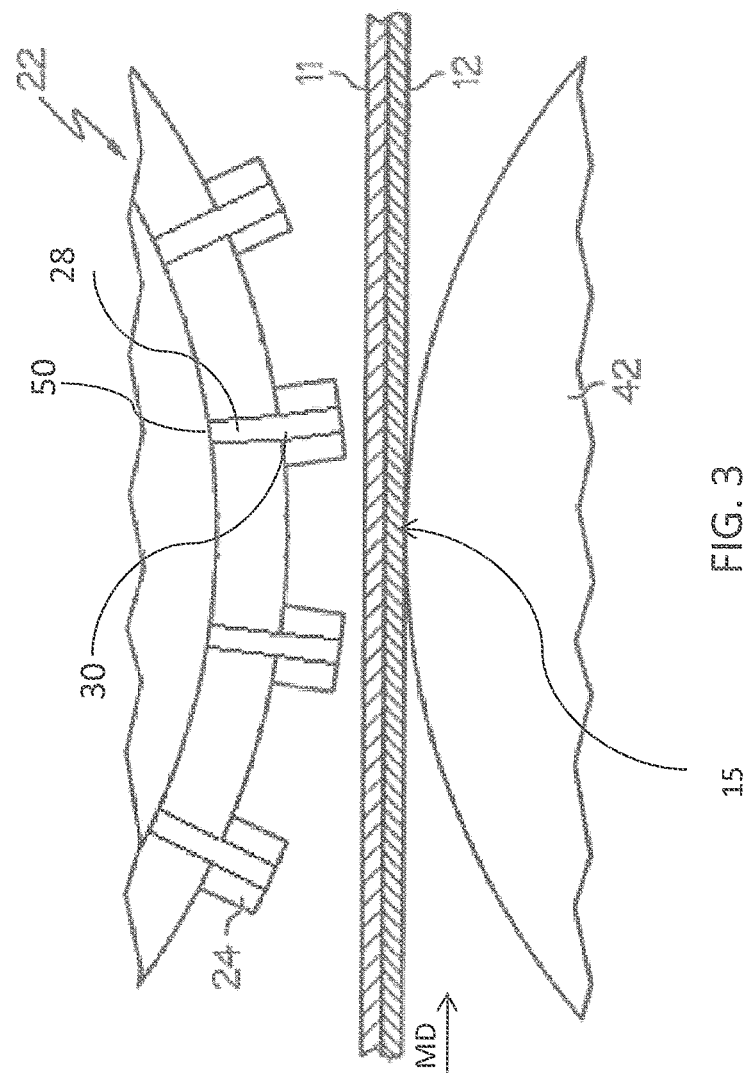
FIG. 3 is a detailed view of the rotary apparatus of FIG. 2.

Referring to FIG. 3, a simplified and partially sectioned view of the forming cylinder 22 with a representative pressure applying member 24 is shown. The pressure applying member 24 may include, for example, a conical or cylindrical shaped fluid outlet 28 through which the heated fluid required to at least partially melt the meltable components of the substrate portions 11, 12 is directed. Although the following discussion refers to a cylindrical shaped fluid outlet 28, it is to be appreciated that fluid outlets 28 having various other shapes may be used, such as for example cones, boxes, and pyramids. A fluid jet nozzle may be connected to a top face 50 of the fluid outlet 28. It is to be appreciated that the top face 50 and orifice 30 may be configured to have various different sizes. For example, in some embodiments, the diameter of top face 50 of the cylindrical shaped fluid outlet 28 may range from 1 millimeter to 8 millimeters and the diameter of orifice 30 of cylindrical shaped zone 34 may range from 0.1 millimeters to 6 millimeters.

Heated fluid passing through the fluid outlet 28 is directed toward an area of overlap 15 of substrate portions 11, 12 as the substrate portions 11, 12 advance in the machine direction MD through the nip 40 between the forming cylinder 22 and an anvil cylinder 42. After the heated fluid partially melts meltable components of the substrate portions 11, 12, the pressure applying member 24 applies pressure and compresses the partially melted components of the substrate portions 11, 12 to join the substrate portions 11, 12 at seam 10. As previously mentioned, the fluid may include ambient air or other gases. It is to be appreciated that the fluid may be heated to various temperatures and pressurized to various pressures. For example, in some embodiments, the fluid may be heated up to a temperature ranging from the lower melting point of substrate portions 11, 12 minus 30° C. to the lower melting point of substrate portions 11, 12 plus 100° C. In some example configurations, the fluid pressure may range from $0.1 \times 10^5$ Newtons per square meter to $1 \times 10^6$ Newtons per square meter.

During operation, the fluid outlet 28 may move with the same speed or approximately the same speed as the area of overlap 15 of the substrate portions 11, 12 for various time intervals to allow the heated fluid to be directed toward at least one outer surface 13, 14. In some embodiments, the heated fluid may be directed toward at least one outer surface 13, 14 for a time interval ranging from 10 to 1000 milliseconds or greater. Shorter or greater time intervals may be used. It is to be appreciated that the pressure applying members 24 on the forming cylinder 22 may be disposed in a predetermined pattern, with each pressure applying member 24 being configured and disposed to apply pressure or compress the substrate portions 11, 12 together after the substrate portions 11, 12 have been at least partially melted by the heated fluid. In some embodiments, the forming cylinder 22 may have pressure applying members 24 which extend circumferentially about each end of the forming cylinder 22.

Anvil cylinder 42 may be a smooth-surfaced, right circular cylinder of steel, which can be independently power-rotated by a speed controlled direct current motor. The anvil cylinder 42 may also be rough-surfaced to form a textured bond. In some configurations, the anvil cylinder 42 may move with the same speed as substrate portions 11, 12 at the area of overlap 15. During this time, the area of overlap 15 may be deformed using the pressure applying member 24, whereby joining occurs and cooling follows. In some embodiments, the anvil cylinder 42 and the pressure applying member 24 may be coated to prevent the substrate portions 11, 12 from sticking to the anvil cylinder 42 and the pressure applying member 24. It is to be appreciated that the anvil cylinder 42 and the pressure applying member 24 may be coated with, for example, a plasma coating, polytetrafluroethylene, or silicone.

In some embodiments, cylinder actuators 43, 45 are provided to drive the forming cylinder 22 and anvil cylinder 42, such as shown in FIG. 2. In addition, there may be a predetermined but adjustable relationship between the surface velocities of the forming cylinder 22 and the anvil cylinder 42. Such a relationship can be synchronous, or asynchronous, that is, with equal surface velocities or with a predetermined surface velocity differential with either the forming cylinder 22 or the anvil cylinder 42 being driven faster than the other. The driving rolls 38 may be driven at surface velocities which maintain predetermined levels of tension or stretch so that neither slack substrate conditions nor excessively tensioned/stretched substrates precipitate undesirable consequences. Nine drive rolls 38 are shown in FIG. 2, however, it should be understood that more or fewer drive rolls may be used. In some embodiments, no drive rolls 38 may be needed, as substrate portions 11, 12, and the joined substrates may be driven by elements incorporated into the forming cylinder 22 and/or the anvil cylinder 42 or by other functional equipment upstream or downstream of apparatus 20.

Figure 4:
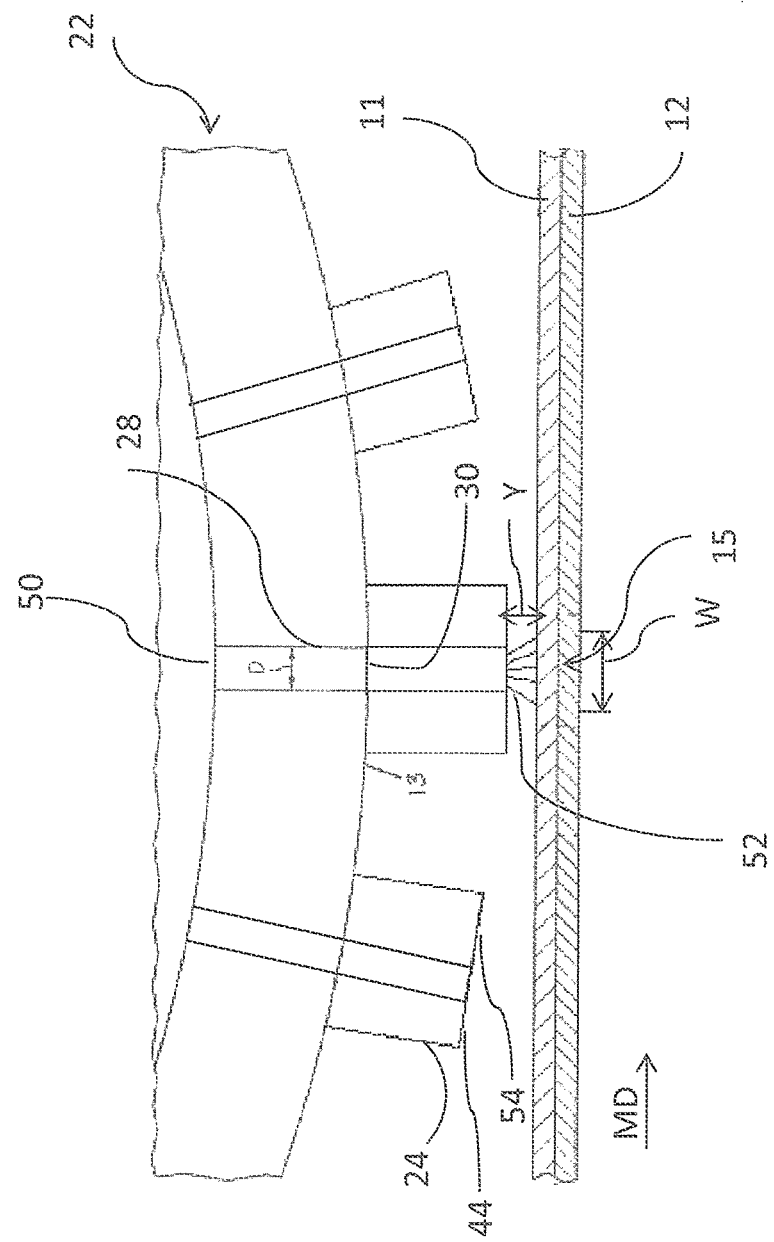
FIG. 4 is another detail view of the rotary apparatus of FIG. 2.
Figure 4A:
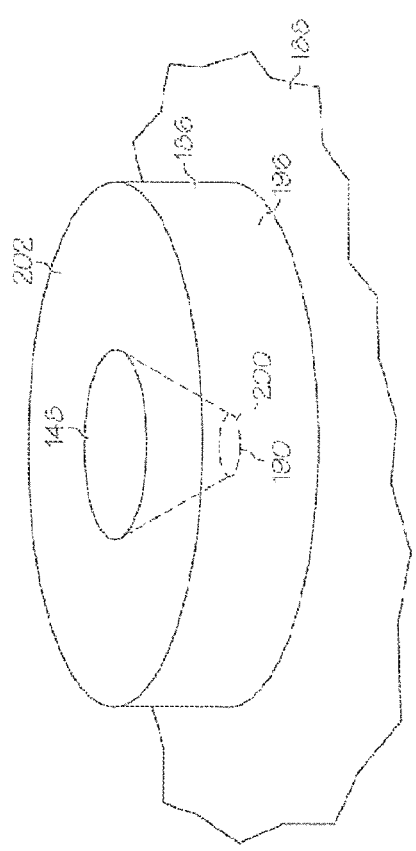
FIG. 4A is a perspective view of an embodiment of a pressure applying member and fluid outlet.

With reference to FIG. 2 and FIG. 4, a seaming operation is shown wherein the substrate portions 11 and 12 advance in the machine direction MD onto the outer circumferential surface 26 of the forming cylinder 22. As shown in FIG. 4, a jet 52 of heated fluid is directed toward the substrate portions 11 and 12 at the overlap area 15. In some embodiments, the jet 52 of heated fluid may distribute in the machine direction MD and/or cross direction CD as the heated fluid is directed toward the substrate portions 11 and 12 forming substantially a cone shape such that the width W at the base of the jet 52 is greater than the diameter D of the fluid orifice 30. While the jet 52 may be a cone shape, other spray patterns are possible, such as for example, cylindrical, fan-shaped, and which may depend, at least in part, on the shape of the fluid orifice 30 and fluid outlet 28, the pressure of the fluid and type of fluid being used.

With continued reference to FIG. 4, in some embodiments, the substrate portions 11 and 12 may be maintained a preselected distance Y from the fluid orifice 30, for example, using the pressure applying member 24. The pressure applying member 24 may be positioned to limit vertical movement of the substrate portions 11 and 12 toward and/or away from the fluid orifice 30 as the substrate portions 11 and 12 are heated during the seaming operation. In some embodiments, the distance Y between the outer surface 13 of the substrate portion 11 facing the fluid orifice 30 may be between about 0 mm and about 20 mm, such as between about 0 mm and about 5 mm, such as between about 0.5 mm and about 3 mm. The distance Y between the outer surface 13 of the substrate portion 11 facing the fluid orifice 30 may be maintained within 3 mm of the preselected distance Y. Control of the distance Y may also result in a relatively more predictable fluid spray and melt pattern during the heating process.

In some embodiments, the forming cylinder 22 may be rotating at a constant speed, decreasing speed, increasing speed, or may be stationary while the jet 52 of heated fluid at least partially melts the substrate portions 11 and 12. Once the substrate portions 11 and 12 are at least partially melted, the pressure applying surface 44 of the pressure applying member 24 contacts the substrate portions 11 and 12 at the overlapping, at least partially melted area 15. The pressure applying member 24 compresses the substrate portions 11 and 12 together between the pressure applying surface 44 and the anvil cylinder 42. While a single fluid outlet 28 and jet 52 are illustrated in FIG. 4, multiple fluid outlets may be provided, for example, such that multiple jets of heated fluid may be used to at least partially melt the substrate portions 11 and 12.

In some embodiments, a position control member may be used to maintain the absorbent articles within a constant distance from the outer circumferential surface of the forming cylinder as the fluid is heating the overlap area. The position control device may be positioned to limit vertical movement of the substrate portions and toward and/or away from the fluid orifice as during the seaming operation. In some embodiments, the position control member may be a belt. The position control member may be located adjacent the forming cylinder and may take the shape of at least a portion of the forming cylinder. The position control member may hold the substrates in the range of 0 millimeters to about 10 millimeters from the forming cylinder, or between about 0.5 millimeters to about 5 millimeters from the forming cylinder.

Figure 5:
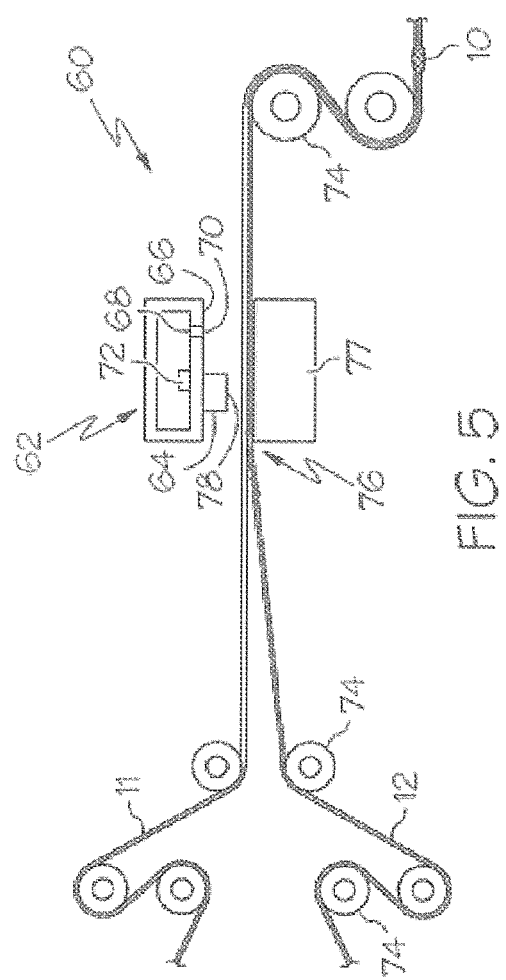
FIG. 5 is a simplified, schematic drawing of another embodiment of a seaming apparatus useful for joining two or more substrate portions.

FIG. 5 shows an embodiment of a translational seaming apparatus 60 that may be used for joining the substrate portions 11 and 12 to form the seam 10. The translational seaming apparatus 60 includes a forming block 62 (shown diagrammatically in section) with a pressure applying member 64 extending outwardly from a face 66 of the forming block 62. While a single pressure applying member 64 is illustrated, there may be more than one pressure applying member. Adjacent and spaced laterally from the pressure applying member 64 is a fluid outlet 68 including a fluid orifice 70. The fluid outlet 68 is in fluid communication with a fluid chamber 71 providing a pressurized fluid source for delivery of heated, pressurized fluid to the fluid outlet 68. A heating device 72 may be provided for heating the fluid within the fluid chamber 70. In some embodiments, a valve may control egress of fluid from the fluid chamber 70 and into the fluid outlet 68.

Similar to the apparatus 20 described above, driving rolls 74 may be used for supplying the substrate portions 11 and 12 to an opening 76 between the forming block 62 and an anvil block 77. The anvil block 76 is positioned to allow a pressure applying surface 78 of the pressure applying member 64 to compress the substrate portions 11 and 12 together at the area of overlap 15. As discussed above, a position control member may be used to maintain the absorbent articles within a constant distance from the forming block as the fluid is heating the overlap area. The position control member may hold the substrates in the range of 0 millimeters to about 20 millimeters from the forming block, or between about 0.5 millimeters to about 5 millimeters from the forming block.

A seaming operation is shown in FIGS. 6A and 6B, wherein the substrate portions 11 and 12 advance in the machine direction MD through the opening 76 between the forming block 62 and the anvil block (not shown for clarity). A jet 84 of heated fluid (e.g., air) is directed toward the substrate portions 11 and 12 at the overlap area 15. As can be seen by FIG. 6A, the jet 84 of heated fluid may distribute in the machine direction MD and cross direction CD as it approaches the substrate portions 11 and 12 forming substantially a cone shape such that the width W at the base of the jet 84 is greater than the diameter D of the fluid orifice 70. While the jet 84 may be a cone shape, other spray patterns are possible, such as cylindrical, fan-shaped, etc., which may depend, at least in part, on the shape of the fluid orifice 70 and fluid outlet 68, the pressure of the fluid and type of fluid being used.

The substrate portions 11 and 12 may be maintained a preselected distance Y from the fluid orifice 70, for example, using a position control device. In some embodiments, the distance Y between the outer surface 13 of the substrate portion 11 facing the fluid orifice 30 may be between about 0 mm and about 20 mm; between about 0 mm and about 5 mm; or between about 0.5 and about 3 mm. Control of the distance Y may also result in a relatively more predictable fluid spray and melt pattern during the heating process.

The pressure applying member 64 and the fluid orifice 70 may also be separated from each other. For example, as shown FIGS. 6A and 6B, the fluid orifice 70 is offset laterally from the pressure applying member 64. The fluid orifice 70 may be offset from the pressure applying member a distance such that the pressure applying member 64 does not intersect the jet 84 at any portion along the distance Y. Additionally, the pressure applying surface 78 of the pressure applying member 64 is spaced away from the substrate portions 11 and 12 during the heating operation. Thus, the pressure applying member 64 does not interfere with the heating of the substrate portions 11 and 12 by the jet 84 of heated fluid.

The forming block 62 may be moving at a constant speed, decreasing speed, increasing speed, or may be stationary while the jet 84 of heated fluid at least partially melts the substrate portions 11 and 12. Once the substrate portions 11 and 12 are at least partially melted, the forming block 62 may move toward the substrate portions 11 and 12 (both in the machine direction MD and vertically as shown by arrows 65 and 67) and the pressure applying surface 78 of the pressure applying member 64 contacts the substrate portions 11 and 12 at the overlapping, at least partially melted area 15. The pressure applying member 64 compresses the substrate portions 11 and 12 together between the pressure applying surface 78 and the anvil block 76.

FIG. 7 illustrates another translational seaming apparatus 90 that may be used for joining the substrate portions 11 and 12 to form the seam 10. A forming block 92 includes many of the same or similar features as forming block 62 shown in FIG. 5, including a pressure applying member 94 extending outwardly from a face 96 of the forming block 92 and a fluid outlet 98 including a fluid orifice 100 that is spaced from the pressure applying member 94. The fluid outlet 98 is in fluid communication with a fluid chamber 103 providing a pressurized fluid source for delivery of heated, pressurized fluid to the fluid outlet 98.

In the embodiment of FIG. 7, the fluid outlet 98 is arranged at an angle to vertical, such as for example between about 0 and about 75 degrees; between about 30 and 60 degrees; or about 45 degrees. As such, the fluid outlet 98 directs a jet 104 of heated fluid to a location at least partially beneath the pressure applying member 94 with a pressure applying surface 106 of the pressure applying member 94 spaced away from the substrate portions 11 and 12. The pressure applying member 94 and the fluid orifice 100 are separated from each other. In the illustrated example, the fluid orifice 100 is offset laterally from the pressure applying member 94 a distance such that the pressure applying member 100 does not intersect the jet 104 at any portion along the height of the jet 104. Additionally, the pressure applying surface 106 of the pressure applying member 94 is spaced away from the substrate portions 11 and 12 during the heating operation. Thus, the pressure applying member 94 does not interfere with the heating of the substrate portions 11 and 12 by the jet 104 of heated fluid.

The forming block 92 may be stationary while the jet 104 of heated fluid at least partially melts the substrate portions 11 and 12. Once the substrate portions 11 and 12 are at least partially melted, the forming block 92 may move in a vertical direction in the direction of arrows 109 toward the substrate portions 11 and 12 and the pressure applying surface 106 of the pressure applying member 94 contacts the substrate portions 11 and 12 at the overlapping, at least partially melted area 15. The pressure applying member 94 compresses the substrate portions 11 and 12 together between the pressure applying surface 106 and the anvil block.

In some embodiments, it is to be appreciated that the translational seaming apparatuses of FIGS. 6A, 6B, and 7 may be integral with a rotary drum apparatus. For example, the drum may oscillate such that the pressure applying member shifts relative to the substrate portions. A position control device may be used to maintain the absorbent articles within a constant distance from the rotary drum apparatus as the fluid is heating the overlap area. The position control device may be positioned to limit vertical movement of the substrate portions and toward and/or away from the fluid orifice as during the seaming operation. In some embodiments, the position control member may be a belt.

FIG. 8 shows a simplified, diagrammatic drawing of another embodiment of a rotary seaming apparatus 110 that may be used for joining the substrate portions 11 and 12 to form the seam 10. The rotary seaming apparatus 110 includes a heating cylinder 112 (shown diagrammatically in section) with a plurality of fluid outlets 114 disposed about a periphery 116 of the heating cylinder 112. The fluid outlets 114 are each in communication with a fluid chamber 118 providing a pressurized fluid source for delivery of heated, pressurized fluid to the fluid outlets 114. A heating device 120 may be provided for heating the fluid within the fluid chamber 118. In some embodiments, valves may control egress of fluid from the fluid chamber 118 and into the fluid outlets 114.

With continued reference to FIG. 8, the heating cylinder 112 advances the substrate portions 11 and 12 to a nip 122 formed between an anvil cylinder 124 and a pressure applying cylinder 126. The pressure applying cylinder 126 may include a plurality of pressure applying members 128 disposed about a periphery 130 of the pressure applying cylinder 126. In other embodiments, the anvil cylinder 124 may be replaced by the pressure applying cylinder 126.

In operation, the substrate portions 11 and 12 are advanced in the machine direction MD to the periphery 116 of the heating cylinder 112 and travel about the heating cylinder 112 as the heating cylinder 112 rotates. Heated fluid is delivered to the substrate portions 11 and 12 through the plurality of fluid outlets 114 thereby at least partially melting overlapped areas of the substrate portions 11 and 12. Because the substrate portions 11 and 12 travel with the rotating heating cylinder 112, heating of the substrate portions 11 and 12 may be facilitated by matching the travel speed of the substrate portions 11 and 12 with the surface speed of the heating cylinder 112. In some embodiments, the substrate portions 11 and 12 may also travel a predetermined contact angle, such as for example 45 degrees or more, around the periphery 116 of the heating cylinder 112. In some embodiments, the contact angle is selected to allow heating of overlapped areas 15 of the substrate portions 11 and 12 for between about 5 and about 2000 milliseconds, such as between about 10 and about 500 milliseconds, such as between about 20 and about 200 milliseconds.

Once heated, the substrate portions 11 and 12 advance to the nip 122 formed between the rotating anvil cylinder 124 and the rotating pressure applying cylinder 126. As the cylinders 124 and 126 rotate, the substrate portions 11 and 12 are pulled into the nip 122 and the pressure applying members 128 then compress the at least partially melted, overlapping areas 15 thereby forming the seam 10 and joining the substrate portions 11 and 12 together.

Figure 9:
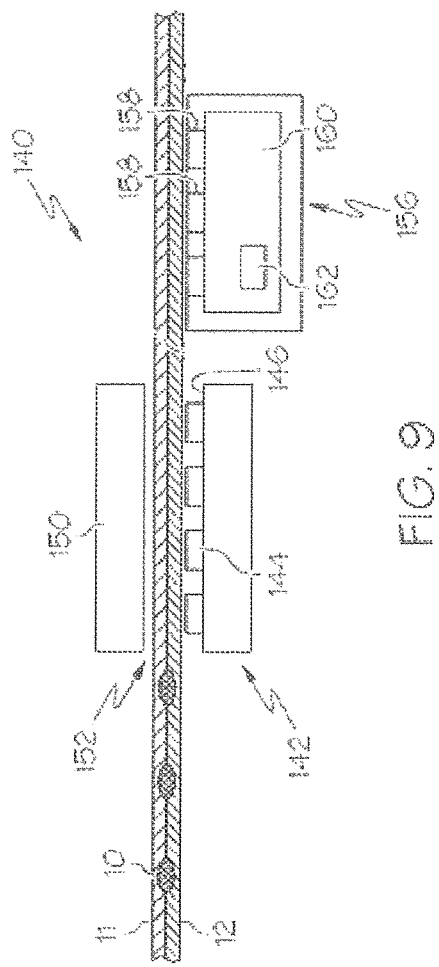
FIG. 9 is a simplified, schematic drawing of another embodiment of a seaming apparatus useful for joining two or more substrate portions.

FIG. 9 shows an embodiment of a traversing seaming apparatus 140 that may be used for joining the substrate portions 11 and 12 to form the seam 10. The traversing seaming apparatus 140 includes a forming block 142 with a plurality of pressure applying members 144 extending outwardly from a face 146 of the forming block 142. Any suitable number of pressure applying members 144 may be utilized. An anvil block 150 is located adjacent the forming block 142 defining a opening 152 therebetween. In some embodiments, the anvil block 150 may be connected to the forming block 142 by any suitable connection that allows the anvil block 150 and/or the forming block 142 to move toward and away from the other. For example, an actuator, such as a pneumatic or a hydraulic actuator, may be provided that moves one or both of the anvil block 150 and the forming block 142 toward and away from one another. In some embodiments, the forming block 142 and the anvil block 150 may be supported separately and one or both may include their own actuator for moving the forming and anvil blocks 142 and 150.

A heating block 156 (shown diagrammatically in section) that includes a plurality of fluid outlets 158 shown in FIG. 9 is adjacent and spaced laterally from the forming and anvil blocks 142 and 150. The fluid outlets 158 are in fluid communication with a fluid chamber 160 providing a pressurized fluid source for delivery of heated, pressurized fluid (e.g., air) to the fluid outlets 158. A heating device 162 may be provided for heating the fluid within the fluid chamber 160. In some embodiments, a valve may control egress of fluid from the fluid chamber 160 and into the fluid outlets 158.

Similar to the apparatus described above, driving rolls (not shown) may be used to advance the substrate portions 11 and 12 in the machine direction MD to the opening 152 between the forming block 142 and the anvil block 150. The anvil block 150 is positioned to allow pressure applying surfaces of the pressure applying members 144 to compress the substrate portions 11 and 12 together at the area of overlap 15.

In operation, the substrate portions 11 and 12 are moved to a position adjacent the heating block 156. Jets of heated fluid are directed toward the substrate portions 11 and 12 at the overlap area 15. As discussed above, the substrate portions 11 and 12 may be maintained a preselected distance from the fluid outlets 158, for example, using a position control device. During the heating operation, the substrate portions 11 and 12 may be stationary for a preselected amount of time to allow for the at least partial melting of the substrate portions 11 and 12 at the overlap areas 15. Once at least partially melted, the substrate portions 11 and 12 may advance to the opening 152 between the forming block 142 and an anvil block 150. One or both of the forming block 142 and the anvil block 150 may be moved toward the other thereby compressing the substrate portions 11 and 12 together at the at least partially melted, overlap areas 15.

Figure 10:
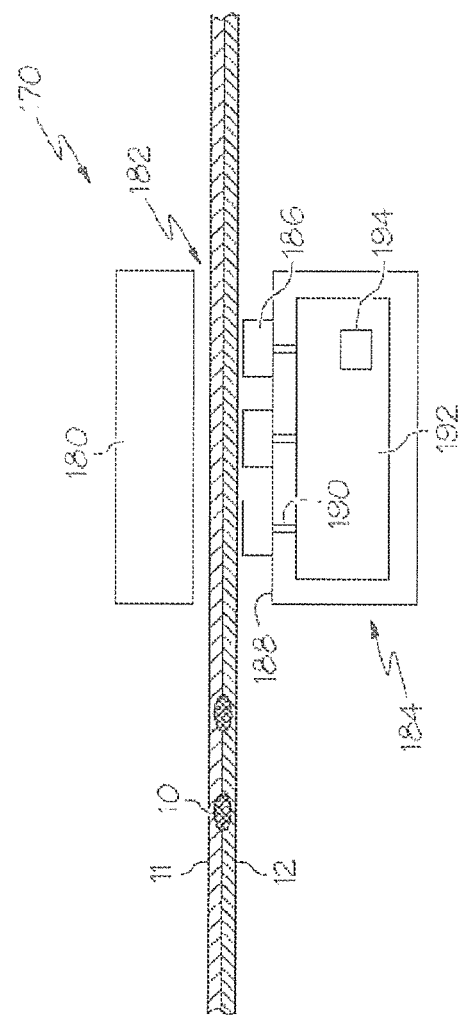
FIG. 10 is a simplified, schematic drawing of another embodiment of a seaming apparatus useful for joining two or more substrate portions.

FIG. 10 shows another embodiment of a traversing seaming apparatus 170 for joining the substrate portions 11 and 12 to form the seam 10. The traversing seaming apparatus 170 includes a heating and forming block 184 (shown diagrammatically in section) and an anvil block 180 forming an opening 182 between the anvil block 180 and the heating and forming block 184. The heating and forming block 184 may include both pressure applying members 186 that extend outwardly from a face 188 of the heating and forming block 184 and fluid outlets 190 that are each in communication with a fluid chamber 192 providing a pressurized fluid source for delivery of heated, pressurized fluid to the fluid outlets 190. A heating device 194 may be provided for heating the fluid within the fluid chamber 192. In some embodiments, valves may control egress of fluid from the fluid chamber 192 and into the fluid outlets 190.

Referring back to FIG. 10, in operation, the substrate portions 11 and 12 are moved to the opening 182 between the heating and forming block 184 and the anvil block 180. Jets of heated fluid are directed toward the substrate portions 11 and 12 at the overlap area 15. As above, the substrate portions 11 and 12 may be maintained a preselected distance from the fluid outlets 190, for example, using a position control device. During the heating operation, the substrate portions 11 and 12 may be stationary for a preselected amount of time to allow for the at least partial melting of the substrate portions 11 and 12 at the overlap areas 15. Once at least partially melted, one or both of the heating and forming block 184 and the anvil block 180 may be moved toward the other thereby compressing the substrate portions 11 and 12 together at the at least partially melted, overlap areas 15.

Figure 11:
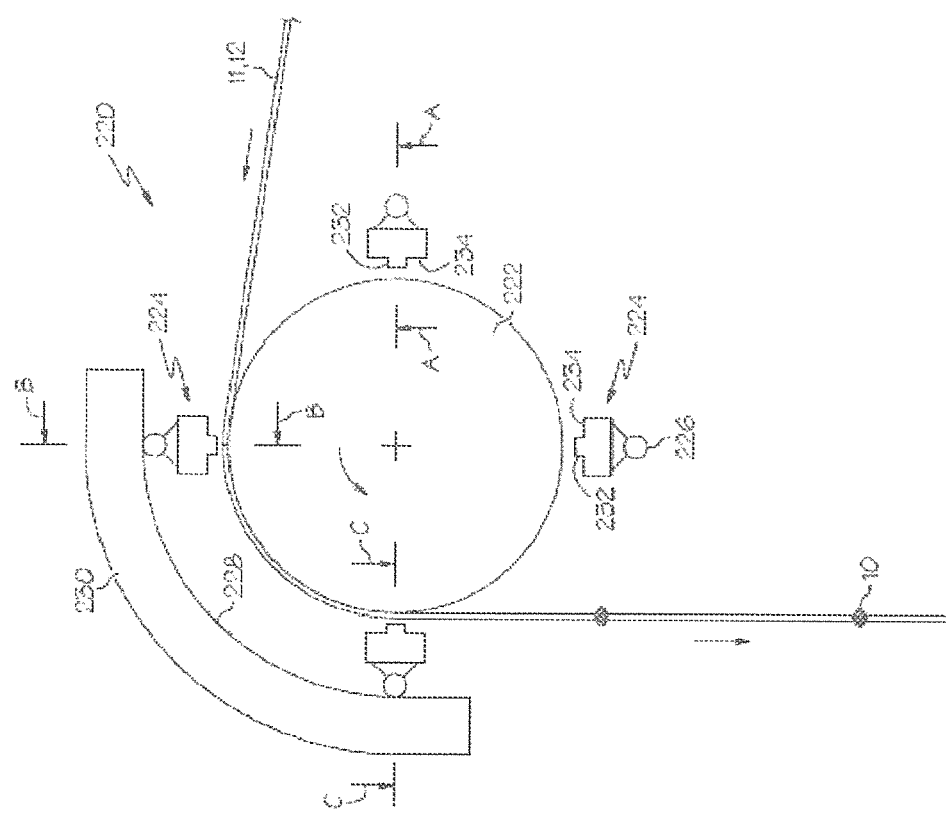
FIG. 11 is a simplified, schematic drawing of another embodiment of a seaming apparatus useful for joining two or more substrate portions.

Although some embodiments have been shown with a fluid outlet located away from and/or apart from the pressure applying member, it is to be appreciated that the fluid outlet may be configured so as to be combined with the pressure applying member. For example, FIG. 11 shows an embodiment with a combination fluid outlet 190 and pressure applying member 186. The pressure applying member 186 includes an outer wall 196 extending outwardly from the face 188 of the heating and forming block 184, an inner wall 198 extending downwardly toward a fluid orifice 200 of the fluid outlet 190 and a pressure applying surface 202 extending between the outer wall 196 and the inner wall 198. As can be seen, the fluid orifice 200 is spaced vertically or recessed behind the pressure applying surface 202. Such an arrangement can help inhibit clogging of the fluid orifice 200, for example, by the substrate material when the pressure applying surface 202 contacts the substrate portions 11 and 12. While the pressure applying member 186 is illustrated as tubular or cylindrical extending around the entire periphery of the fluid outlet 190, other configurations are possible.

Figure 4B:
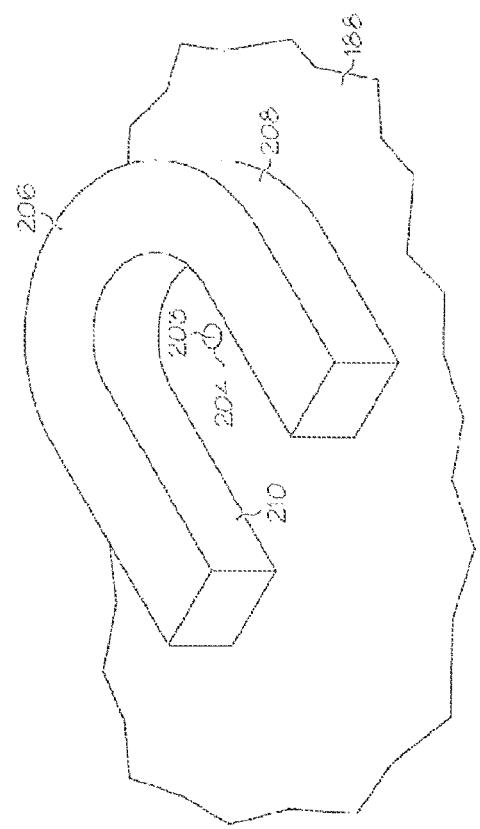
FIG. 4B is a perspective view of another embodiment of a pressure applying member and fluid outlet.

FIG. 4B shows another example of a combination fluid outlet 204 and pressure applying member 206. The pressure applying member 206 includes an outer wall 208 extending outwardly from the face 188 of the heating and forming block 184, an inner wall 210 extending downwardly toward a fluid orifice 203 of the fluid outlet 204 and a pressure applying surface 212 extending between the outer wall 208 and the inner wall 210. As above, the fluid orifice 203 is spaced vertically or recessed behind the pressure applying surface 212. Unlike the pressure applying member 186, however, the pressure applying member 206 is U or horseshoe shaped and extends about only part of fluid outlet 204. Any other suitable shapes may be used, such as irregular shapes, squares, rectangles, etc.

Figure 11A:
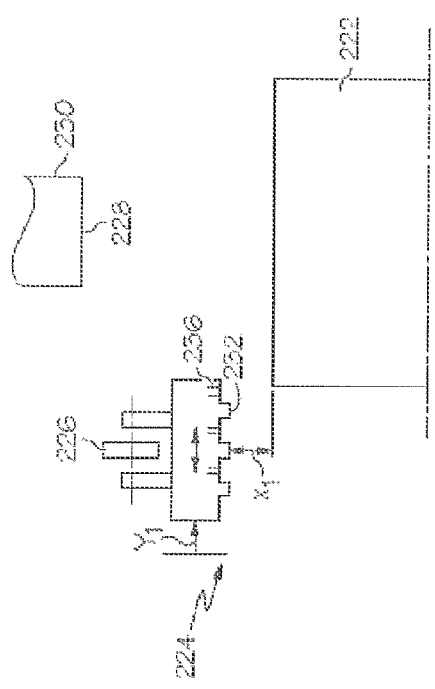
FIG. 11A illustrates the seaming apparatus of FIG. 11 in use.

FIG. 11 shows another embodiment of a traversing seaming apparatus 220 for joining the substrate portions 11 and 12 to form the seam 10. The apparatus 220 includes an anvil cylinder 222 and at least one forming block assembly 224 that rotates with the anvil cylinder 222. The apparatus 220 shown in FIG. 11 includes four forming block assemblies spaced ninety degrees about the periphery of the anvil cylinder 222. Each forming block assembly 224 includes a cam follower 226 that engage a cam surface 228 of a cam member 230 to control movement of the forming block assemblies 224 toward and away from the anvil cylinder 222. As shown in FIG. 11A, the forming block assemblies 224 include a pressure applying member 232 extending outwardly from a face 234 of the block assemblies 224 toward the anvil cylinder 222. The forming block assemblies also include a fluid outlet 236 spaced laterally from the pressure applying member 232 in communication with a fluid chamber providing a pressurized fluid source for delivery of heated, pressurized fluid to the fluid outlets 236.

Figure 11B:
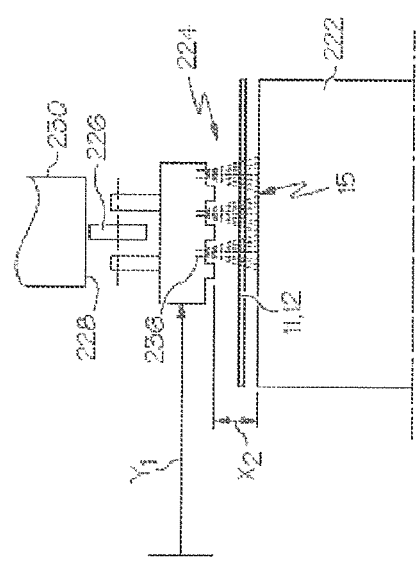
FIG. 11B illustrates the seaming apparatus of FIG. 11 in use.

With continued reference to FIG. 11A, the block assembly 224 rotates with the anvil cylinder 222 at a location adjacent the anvil cylinder 222 and spaced radially away a distance $X_1$ from the periphery of the anvil cylinder 222. The substrate portions 11 and 12 are advanced in the machine direction MD to the periphery of the anvil cylinder 222 as the anvil cylinder 222 rotates. As shown in FIG. 11B, the block assembly 224 moves laterally a distance $Y_1$ to a location above the periphery of the anvil cylinder 222 and the substrate portions 11 and 12. The cam follower 226 engages the cam surface 228 of the cam member 230 which controllably moves the block assembly 224 toward the substrate portions 11 and 12 a distance $X_2$ from the periphery of the anvil cylinder 222.

Figure 11C:
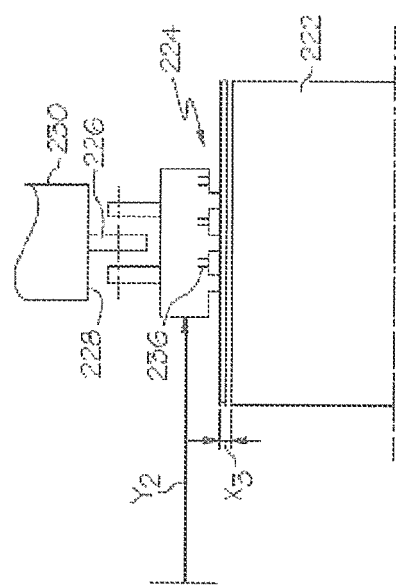
FIG. 11C illustrates the seaming apparatus of FIG. 11 in use.

Jets of heated fluid are directed toward the substrate portions 11 and 12 at the overlap area 15. As previously discussed, the substrate portions 11 and 12 may be maintained a preselected distance from the fluid outlets 236 using the cam surface 228. During the heating operation, the substrate portions 11 and 12 may move together, or at substantially the same rate, to allow for the at least partial melting of the substrate portions 11 and 12 at the overlap areas 15. Once at least partially melted, the block assembly 224 may advance to a distance $Y_2$ as shown in FIG. 11C. The forming block assembly 224 may also move toward the periphery of the anvil cylinder 222 to a distance $X_3$ thereby compressing the substrate portions 11 and 12 together at the at least partially melted, overlap areas 15.

The following addresses some distinctions with respect to the melting temperatures of the layers in the seam. If one or more layers had a substantially different melting temperature than another layer or layers, the air temperature, the length of time the materials are exposed to the heated air, or both, may be adjusted to accommodate the highest melting temperature in the seam. It has been found that in some instances, selecting seam materials for like melting temperatures, a seam between substrates of like melting temperature may provide more consistent bonds.

Using substrate portions of like melting temperature may also provide processing benefits. When the process parameters are adjusted for a relatively high melting temperature, substrates in the seam having a lower melting temperature may be damaged during processing. To help limit such damage, a relatively small orifice may be used to confine the flow of hot air to a limited area. Using more moderate temperatures and dwell times, relative to the melting temperatures of the substrates in the seam, it may be possible to use a larger orifice. A larger orifice may be less prone to tool contamination, and therefore require less frequent or less intense cleaning and maintenance. Further, it may be possible to reduce the dwell times that the seam materials are exposed to hot air, resulting in faster processing.

As previously mentioned, the processes and apparatuses discussed herein may be used to bond various types of substrate configurations, some of which may be used in the manufacture of different types of absorbent articles. To help provide additional context to the subsequent discussion of the process embodiments, the following provides a general description of absorbent articles in the form of diapers that include components that may be bonded in accordance with the methods and apparatuses disclosed herein.

Figure 12:
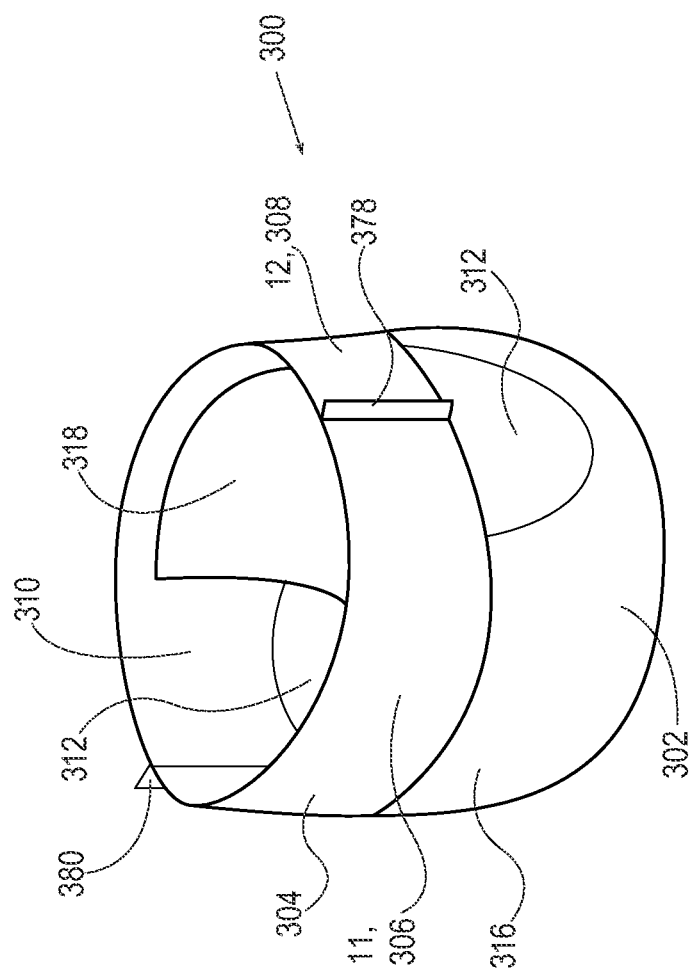
FIG. 12 is a perspective view of a diaper pant.

FIGS. 12 and 13 show an example of a diaper pant 300 that may be assembled and folded in accordance with the apparatuses and methods disclosed herein. In particular, FIG. 12 shows a perspective view of a diaper pant 300 in a pre-fastened configuration, and FIG. 13 shows a plan view of the diaper pant 300 with the portion of the diaper that faces away from a wearer oriented toward the viewer. The diaper pant 300 shown in FIGS. 12 and 13 includes a chassis 302 and first and second substrate portions 11 and 12, forming a ring-like elastic belt 304. As discussed below in more detail, the first substrate portion 11 in the form of a first elastic belt 306 and the second substrate portion 12 in the form of a second elastic belt 308 are connected together to form the ring-like elastic belt 304.

With continued reference to FIG. 13, the chassis 302 includes a first waist region 316, a second waist region 318, and a crotch region 320 disposed intermediate the first and second waist regions. The first waist region 316 may be configured as a front waist region, and the second waist region 318 may be configured as back waist region. In some embodiments, the length of each of the front waist region, back waist region, and crotch region may be ⅓ of the length of the absorbent article 300. The diaper 300 may also include a laterally extending front waist edge 321 in the front waist region 316 and a longitudinally opposing and laterally extending back waist edge 322 in the back waist region 318. To provide a frame of reference for the present discussion, the diaper 300 and chassis 302 of FIG. 13 are shown with a longitudinal axis 324 and a lateral axis 326. In some embodiments, the longitudinal axis 324 may extend through the front waist edge 321 and through the back waist edge 322. And the lateral axis 326 may extend through a first longitudinal or right side edge 328 and through a midpoint of a second longitudinal or left side edge 330 of the chassis 302.

As shown in FIGS. 12 and 13, the diaper pant 300 may include an inner, body facing surface 332, and an outer, garment facing surface 334. The chassis 302 may include a backsheet 336 and a topsheet 338. The chassis 302 may also include an absorbent assembly 340 including an absorbent core 342 may be disposed between a portion of the topsheet 338 and the backsheet 336. As discussed in more detail below, the diaper 300 may also include other features, such as leg elastics and/or leg cuffs to enhance the fit around the legs of the wearer.

As shown in FIG. 13, the periphery of the chassis 302 may be defined by the first longitudinal side edge 328, a second longitudinal side edge 330; a first laterally extending end edge 344 disposed in the first waist region 316; and a second laterally extending end edge 346 disposed in the second waist region 318. Both side edges 328 and 330 extend longitudinally between the first end edge 344 and the second end edge 346. As shown in FIG. 13, the laterally extending end edges 344 and 346 are located longitudinally inward from the laterally extending front waist edge 321 in the front waist region 316 and the laterally extending back waist edge 322 in the back waist region 318. When the diaper pant 300 is worn on the lower torso of a wearer, the front waist edge 321 and the back waist edge 322 of the chassis 302 may encircle a portion of the waist of the wearer. At the same time, the chassis side edges 328 and 130 may encircle at least a portion of the legs of the wearer. And the crotch region 320 may be generally positioned between the legs of the wearer with the absorbent core 342 extending from the front waist region 316 through the crotch region 320 to the back waist region 318.

It is to also be appreciated that a portion or the whole of the diaper 300 may also be made laterally extensible. The additional extensibility may help allow the diaper 300 to conform to the body of a wearer during movement by the wearer. The additional extensibility may also help, for example, allow the user of the diaper 300 including a chassis 302 having a particular size before extension to extend the front waist region 316, the back waist region 318, or both waist regions of the diaper 300 and/or chassis 302 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

The first and second elastic belts 306, 308 may also each include belt elastic material interposed between the outer layer 362 and the inner layer 364. The belt elastic material may include one or more elastic elements such as strands, ribbons, or panels extending along the lengths of the elastic belts. As shown in FIGS. 13, 15A, and 15B, the belt elastic material may include a plurality of elastic strands 368 which may be referred to herein as outer, waist elastics 370 and inner, waist elastics 372. As shown in FIG. 13, the elastic strands 368 continuously extend laterally between the first and second opposing end regions 306a, 306b of the first elastic belt 306 and between the first and second opposing end regions 308a, 308b of the second elastic belt 308. In some embodiments, some elastic strands 368 may be configured with discontinuities in areas, such as for example, where the first and second elastic belts 306, 308 overlap the absorbent assembly 340. In some embodiments, the elastic strands 368 may be disposed at a constant interval in the longitudinal direction. In other embodiments, the elastic strands 368 may be disposed at different intervals in the longitudinal direction. The belt elastic material in a stretched condition may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt.

It is to be appreciated that the chassis 302 and elastic belts 306, 308 may be configured in different ways other than as depicted in FIG. 13. For example, FIG. 14 shows a plan view of a diaper pant 300 having the same components as described above with reference to FIG. 13, except the first laterally extending end edge 344 of the chassis 302 is aligned along and coincides with the outer lateral edge 307a of the first elastic belt 306, and the second laterally extending end edge 346 is aligned along and coincides with the outer lateral edge 309a of the second belt 308.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for forming a seam, the method comprising the steps of:
    providing an anvil block;
    providing a forming block adjacent the anvil block, the forming block comprising a face, a pressure applying member extending outwardly from the face toward the anvil block, and a fluid outlet extending through a portion of the forming block and spaced laterally from the pressure applying member;
    advancing a first substrate in a machine direction between the forming block and the anvil block with a separation distance between the fluid outlet and the first substrate;
    advancing a second substrate in the machine direction wherein the first substrate is between the second substrate and the forming block;
    controlling the separation distance between the first substrate and the fluid outlet;
    heating a fluid to a temperature sufficient to at least partially melt the substrates;
    directing a jet of the heated fluid through the fluid outlet and onto an overlap area of the first and second substrates;
    partially melting the overlap area;
    moving at least one of the forming block and the anvil block in a machine direction and a vertical direction; and
    compressing the overlap area between the pressure applying member and the anvil block,
    wherein the fluid outlet extends in a direction perpendicular to the machine direction.

2. A method for forming a seam, the method comprising the steps of:
    providing an anvil block;
    providing a forming block adjacent the anvil block, the forming block comprising a face, a pressure applying member extending outwardly from the face toward the anvil block, and a fluid outlet extending through the pressure applying member;
    advancing a first substrate in a machine direction between the forming block and the anvil block with a separation distance between the fluid outlet and the first substrate;
    advancing a second substrate in the machine direction wherein the first substrate is between the second substrate and the forming block;
    controlling the separation distance between the first substrate and the fluid outlet;
    heating a fluid to a temperature sufficient to at least partially melt the substrates;
    directing a jet of the heated fluid through the fluid outlet and onto an overlap area of the first and second substrates;
    partially melting the overlap area;
    moving the forming block in the machine direction toward the overlap area; and
    thereafter compressing the overlap area between the pressure applying member and the anvil block.

3. The method of claim 2, wherein the jet of heated fluid is at a temperature ranging from a lower melting point of the first and second substrates minus 30° C. to the lower melting point of the first and second substrates plus 100° C.

4. The method of claim 2, wherein the jet of heated fluid is directed at the first and second substrates at a pressure in the range of about $0.1 \times 10^5$ Newtons per square meter to about $1 \times 10^6$ Newtons per square meter.

5. The method of claim 2, wherein the fluid is ambient air.

* * * * *